(12) United States Patent
Minder

(10) Patent No.: US 10,867,262 B2
(45) Date of Patent: Dec. 15, 2020

(54) METHOD FOR VALIDATING A RESOURCE FOR A LAB TASK SCHEDULE OF A LABORATORY DEVICE

(71) Applicant: Roche Molecular Systems, Inc., Pleasanton, CA (US)

(72) Inventor: Raymond Minder, Inwil (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 1331 days.

(21) Appl. No.: 14/834,136

(22) Filed: Aug. 24, 2015

(65) Prior Publication Data

US 2016/0063217 A1 Mar. 3, 2016

(30) Foreign Application Priority Data

Aug. 27, 2014 (EP) .................................... 14182372

(51) Int. Cl.
*G06Q 10/06* (2012.01)
*G16H 10/40* (2018.01)

(52) U.S. Cl.
CPC ....... *G06Q 10/06311* (2013.01); *G16H 10/40* (2018.01)

(58) Field of Classification Search
CPC ........ G16H 10/40; G16H 40/20; G16H 10/60; G06Q 10/06; G06Q 10/10; G06Q 10/06311; G06Q 10/063114; G06Q 10/063116
See application file for complete search history.

(56) References Cited

U.S. PATENT DOCUMENTS

| | | | |
|---|---|---|---|
| 8,606,525 B2 | 12/2013 | Jacobs | |
| 2011/0022331 A1* | 1/2011 | Clinton | ..................... B01L 3/54 702/27 |
| 2011/0054946 A1* | 3/2011 | Coulter | .................. G06Q 10/06 705/3 |
| 2011/0143947 A1 | 6/2011 | Chamberlin et al. | |
| 2012/0145778 A1 | 6/2012 | Cong et al. | |
| 2015/0324230 A1 | 11/2015 | Xu et al. | |

FOREIGN PATENT DOCUMENTS

| | | |
|---|---|---|
| CN | 101557345 A | 10/2009 |
| EP | 2037281 A2 | 3/2009 |
| EP | 1772736 B1 | 7/2013 |
| JP | 2010164332 A | 7/2010 |
| JP | 2010175395 A | 8/2010 |
| WO | WO199526535 A1 | 10/1995 |
| WO | WO2011017082 A3 | 5/2011 |
| WO | 2012015809 A2 | 2/2012 |

\* cited by examiner

*Primary Examiner* — Maroun P Kanaan
(74) *Attorney, Agent, or Firm* — Maneesh Gupta; Pamela C. Ancona; M. Reza Savari

(57) ABSTRACT

A method and a laboratory device for validating a resource for a lab task schedule of a laboratory device, the lab task schedule including at least one lab task, the method including the steps of: identifying a resource upon being loaded onto the laboratory device; retrieving resource validity data (RVD) corresponding to the identified resource; retrieving an expected lab task completion time (CT) corresponding to each lab task of the lab task schedule; validating of the resource validity data (RVD) against the expected lab task completion time (CT) corresponding to one or more lab task(s) of the lab task schedule; and generating a resource validation signal indicative of a result of the validation of the resource validity data (RVD).

16 Claims, 2 Drawing Sheets

METHOD FOR VALIDATING A RESOURCE FOR A LAB TASK SCHEDULE OF A LABORATORY DEVICE

CROSS-REFERENCES TO RELATED APPLICATIONS

The present application claims the benefit of priority under 35 U.S.C. § 119 of EP14182372.4, filed Aug. 27, 2014, the content of which is incorporated by reference herein in its entirety.

FIELD OF THE INVENTION

The present disclosure relates to the field of analytics, and in particular to methods for validating a resource for a lab task schedule of a laboratory device, and further to a laboratory device configured to validate a resource for a lab task schedule.

BACKGROUND OF THE INVENTION

Laboratory devices such as automated, semi-automated or manual devices for use in laboratory work in the clinical, chemical, biological, immunology or pharmaceutical area or the like require resources for performing various tasks such as an assay, a sample preparation process, a purification process, a lysis or the like. However most resources have resource limits defined as resource validity data such as an expiry date and time, an onboard stability time, and open stability time. A resource with at least one of such resource limits exceeded is called an invalid resource.

A laboratory device using an invalid resource(s), i.e., with at least one of the resource limits exceeded will produce potentially unreliable results that may not be valid according to laboratory standards. For this reason regulatory requirements may require that results obtained by the use of at least one invalid resource to be invalidated/flagged.

In order to avoid waste of source(s) and/or sample(s) and/or productive time of the laboratory, known laboratory devices are configured to check the validity of the resources as these are loaded onto the laboratory device and/or prior to starting of a lab task.

Nevertheless using known laboratory devices, it can happen that resource limits are exceeded during sample preparation or analysis schedule, triggering one or more of the following problems:

- Flagging of valuable samples as invalid, samples which can potentially not be re-analyzed (e.g. for lack of sufficient sample volume);
- Waste of resources if resources with different resource limits are combined for a lab task, and valid resources are used in combination with invalid resources until the end of the lab task—or even worse up to completion of the entire lab task schedule, a single invalid resource will invalidate the entire process even though other resources are valid;
- Waste of valuable time and reduced productivity of lab tasks because laboratory device(s) can be loaded/blocked with potentially invalid resources.

Aspects of the disclosed method and laboratory device configured to implement the method are therefore to avoid loss of samples, waste of resources and/or increase of productivity.

SUMMARY OF THE INVENTION

The above-identified aspect(s) are addressed according to the disclosed embodiments by forward validation of resource validity against expected completion time(s) of lab tasks that are scheduled for a laboratory device.

In one embodiment, a method is provided for validating a resource for a lab task schedule of a laboratory device, including:

- identifying a resource upon being loaded onto the laboratory device;
- retrieving resource validity data corresponding to the identified resource;
- retrieving an expected lab task completion time corresponding to each lab task of the lab task schedule;
- validating of the resource validity data against the expected lab task completion time corresponding to one or more lab task(s) of the lab task schedule; and
- generating a resource validation signal indicative of a result of the validation of the resource validity data.

According to certain embodiments, the forward validation of the resource validity results in full resource rejection, partial resource acceptance or full resource acceptance. A resource is fully rejected if validation of the resource validity data is unsuccessful for each lab task(s), indicative that the resource is not valid for any of the lab task(s) of the lab task schedule. On the other hand, if the validation of the resource validity data is successful for at least one lab task, indicative that the resource is valid for one or more of the lab task(s) of the lab task schedule, the resource is not fully rejected but partially accepted, leaving the option open for the resource to be loaded into the laboratory device and be allocated for lab tasks for which it is valid up to their respective expected completion time. Finally, if validation of the resource validity data is successful for each lab task, indicative that the resource is valid for each lab task(s) of the lab task schedule, then the resource is fully accepted.

According to particular embodiments, expiration date/time and/or onboard stability time and/or open stability time of the resource(s) is validated against the expected lab task completion time, the expected onboard time respectively the expected lab task processing time corresponding to the lab tasks of the lab task schedule.

According to particular embodiments, the resource validity data of the resources is validated:

- upon loading of the resource onto the laboratory device; and/or
- at any time between loading of the resource and start of one or more lab task(s); and/or
- upon a change in the lab task schedule; and/or
- upon a change in the expected lab task completion time of at least one lab task; and/or
- upon a change of state of the laboratory device having a potential effect on the expected lab task completion time of at least one lab task, such as a defective channel affecting throughput; and/or
- upon a change of state of the laboratory device having a potential effect on the resource validity data, such as a change in storage temperature and/or humidity of the resource.

Embodiment(s) disclosed herein are advantageous as invalidation of valuable samples and/or waste of resources can be avoided while at the same time the productivity of the laboratory device may be improved.

BRIEF DESCRIPTION OF THE FIGURES

Other and further objects, features and advantages of the embodiments will appear more fully from the following description. The accompanying drawings, together with the general description given above and the detailed description given below, serve to explain the principles of the embodiments.

DETAILED DESCRIPTION OF THE INVENTION

Figure 1:
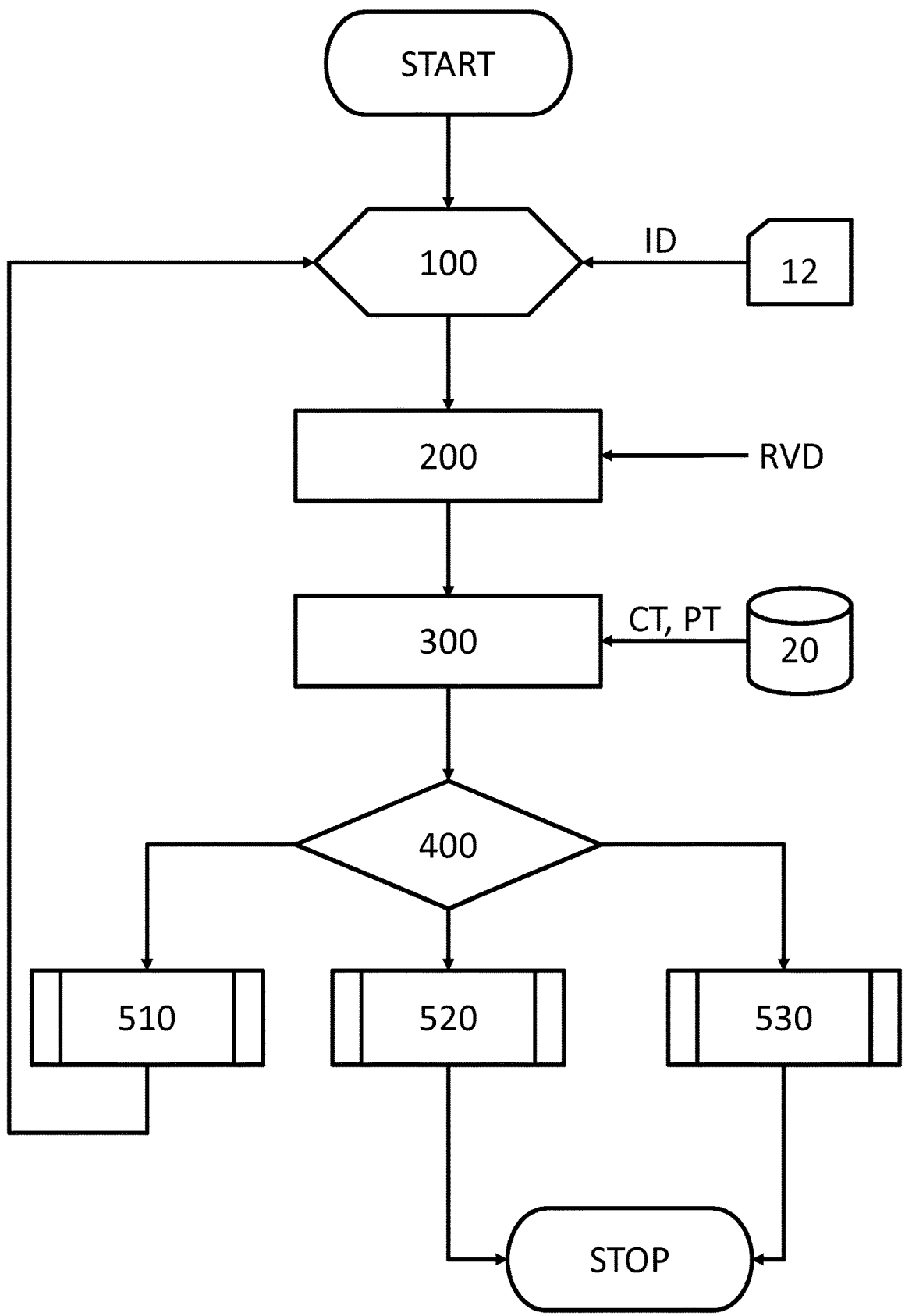
FIG. 1 shows a flowchart illustrating steps of an embodiment of the disclosed method.

By way of illustration, specific exemplary embodiments in which the disclosed subject matter may be practiced now are described.

Certain terms will be used in this patent application, the formulation of which should not be interpreted to be limited by the specific term chosen, but as to relate to the general concept behind the specific term.

The term "laboratory device" as used herein refers to any kind of automated, semi-automated or manual device for use in laboratory work in the clinical, chemical, biological, immunology or pharmaceutical area or the like. Such a laboratory device may comprise, amongst others, at least one of an analyzer, a pipettor, a stirrer, a tempering device, a shaker, or an agitator or the like.

The term "lab task" as used herein refers to any kind of task/process/procedure/etc. of a laboratory device, such as but not limited to:
  an assay, i.e. an investigative/analytic procedure in laboratory medicine for qualitatively assessing or quantitatively measuring the presence or amount or the functional activity of an analyte;
  a purification process, i.e.
  a lysis.

The term "lab task schedule" as used herein refers to any collection of one or more lab tasks assigned to be carried out by a laboratory device at predefined times. A lab task schedule is a list of lab tasks together with scheduled start times and expected completion times. A lab task schedule may also comprise an (inter)dependency of lab tasks, i.e. the start of one lab task may be dependent on completion of a different lab task. It shall be noted that while a lab task schedule is in most occasions predefined, unforeseen events—such as high priority lab tasks—might affect a lab task schedule during processing of a lab task. Therefore a lab task schedule may according to particular embodiments be a dynamic schedule of lab tasks.

The term "RFID tag" as used herein refers to either an active or passive RFID tag that contains information. An RFID tag or transponder includes a coil or antenna and some information stored on an RFID chip that can be read and/or written by an RFID reader. Correspondingly the RFID tag can be read only or read/write and the information associated with the RFID tag can be hard-coded into the RFID tag at the time of manufacture or at some later time. The information stored on an RFID tag includes at least a unique identifier UID.

The term "RFID reader" as used herein includes devices that can read information from and/or write information into an MID tag. RFID readers comprise or are connected to a reader antenna and circuitry to transmit and receive signals with the antenna. The RFID reader antenna generates an electromagnetic field, thereby transferring energy to the tag. Depending on the design of the tag, a portion of the energy transferred to the tag will be reflected to the reader so as to provide information about the tag back to the reader.

The term "resource" as used herein refers to reagent(s)/reagent cassette(s) or consumable(s) of a laboratory device. The term "reagent" is used to indicate a composition required for treatment of a sample. Reagents may be any liquid, e.g. a solvent or chemical solution, which needs to be mixed with a sample and/or other reagent in order e.g. for a reaction to occur, or to enable detection. A reagent may be for example a diluting liquid, including water, it may comprise an organic solvent, it may comprise a detergent, it may be a buffer. Reagents may also be dry reagents adapted e.g. to be dissolved by a sample, another reagent or a diluting liquid. A reagent in the more strict sense of the term may be a liquid solution containing a reactant, typically a compound or agent capable e.g. of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, etc, A. "reagent cassette" can refer to a container comprising a liquid or suspension of reagents. Or a reagent cassette can be a holder for holding containers comprising a liquid or a suspension of reagents.

A "consumable" is understood to be a device which is introduced recurrently to the laboratory device for use in an analytical test. A consumable may be used a single time before being replaced, or it may be use multiple times. Examples of consumables include pipette tips, tip racks, vessels, reagent containers etc.

The term "sample", as used herein, refers to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more diagnostic assays like e.g. clinical chemistry assays, immunoassays, coagulation assays, nucleic acid testing, etc. . . . . The term "sample" as used herein is therefore not only used for the original sample but also relates to a sample which has already been processed (pipetted, diluted, mixed with reagents, enriched, having been purified, having been amplified etc.). As used herein, the term "analyte" refers to the compound or composition to be detected or measured.

Steps of a first embodiment of the method for validating a resource is illustrated on the flowchart of FIG. 1, including:
  100—identifying a resource 12 upon being loaded onto the laboratory device 1;
  200—retrieving resource validity data RVD corresponding to the identified resource 12;
  300—retrieving an expected lab task completion time CT corresponding to each lab task 22 of the lab task schedule 20;
  400—validating of the resource validity data RVD against the expected lab task completion time CT corresponding to one or more lab task(s) 22 of the lab task schedule 20; and

510, 520, 530—generating a resource validation signal indicative of a result of the validation of the resource validity data RVD.

The step 100 of identifying the resource 12 upon being loaded onto the laboratory device 1 is performed by known means of identifying a resource such as a consumable or a reagent. According to one embodiment identification of the resource 12 is by means of an identifier reader 3 such as an RFID reader reading a resource identifier ID such as an RFID tag. The term "upon being loaded" shall be interpreted in a broad meaning, comprising (but not limited to) the loading of the resource 12 into the laboratory device 1; a transfer from a loading station or processing of the resource 12 by an inventory system related to the laboratory device 1.

In step 200, resource validity data RVD corresponding to the identified resource 12 is retrieved. According to one embodiment, the resource validity data RVD is retrieved by the laboratory device 1 from a validity data repository 50 comprised by and/or communicatively connected to the laboratory device 1. Alternatively, according to a further embodiments, the resource validity data RVD is retrieved by the laboratory device 1 from the resource identifier ID, the resource validity data RVD having been previously stored therein. Alternatively, according to an even further embodiment, the resource validity data RVD is retrieved by the laboratory device 1 based on resource data retrieved from the resource identifier ID in combination with task data associated with the lab task 22 and/or the lab task schedule 20.

According to embodiments, the resource validity data RVD includes:
  an expiration date and/or time of the resource 12; and/or
  an onboard stability time of the resource 12; and/or
  an open stability time of the resource 12.

In step 300, an expected lab task completion time CT corresponding to each lab task 22 of the lab task schedule 20 is retrieved. According to one embodiment, the expected lab task completion time CT is retrieved from task data associated with the lab task 22 and/or the lab task schedule 20. Alternatively the expected lab task completion time CT is retrieved from a memory comprised by or communicatively connected to the laboratory device 1. According to a further embodiment, the retrieval of the expected lab task completion time CT comprises a computing of the expected lab task completion time CT based on task data associated with the lab task 22 in view of a task load or expected task load of the laboratory device 1.

In a following step 400, the resource validity data RVD is validated against the expected lab task completion time CT corresponding to one or more lab task(s) 22 of the lab task schedule 20. According to embodiments and depending on the data comprised within the resource validity data RVD, the validation of the resource validity data RVD comprises one or more of the following:
  a comparison of the expiration date and/or time of the resource 12 with the expected lab task completion time CT, the validation being successful if the expected lab task completion time CT does not extend beyond the expiration date and/or time of the resource 12; and/or
  a comparison of the onboard stability time with an expected onboard time ranging from loading of the resource 12 to the expected lab task completion time CT, the validation being successful if the expected onboard time does not extend beyond the onboard stability time of the resource 12; and/or
  a comparison of the open stability time with an expected lab task processing time PT, the validation being successful if the expected lab task processing time PT does not extend beyond the open stability time of the resource 12.

In a following step 510, 520, 530, a resource validation signal indicative of a result of the validation of the resource validity data RVD is generated, the resource validation signal corresponding to the resource 12 being indicative of one of the following:
  full resource rejection 510, generated if validation of the resource validity data RVD is unsuccessful for each lab task(s) 22, indicative that the resource 12 is not valid for any of the lab task(s) 22 of the lab task schedule 20;
  partial resource acceptance 520, generated if validation of the resource validity data RVD is successful for at least one lab task 22, indicative that the resource 12 is valid for one or more of the lab task(s) 22 of the lab task schedule 20;
  full resource acceptance 530, generated if validation of the resource validity data RVD is successful for each lab task 22, indicative that the resource 12 is valid for each lab task(s) 22 of the lab task schedule 20.

In case of full resource rejection 510, according to embodiments, the user of the laboratory device 1 is expected to provide an alternative resource 12 which is valid for at least one lab task 22 so that the lab task schedule 20 can be at least partially carried out. In other words, alternative resources 12 are expected at least until partial resource acceptance 520 is signaled, in which case the corresponding resource 12 is allocated to a lab task 22 for which validation of the resource validity data RVD is successful.

Alternatively, the process scheduler 5 of the laboratory device 1 may be configured such that the entire lab task schedule 20 is halted until a valid resource 12 is provided for each lab task 22 of the lab task schedule 20.

In order to provide flexibility with respect to delays in lab task completion, according to particular embodiment(s), a reserve time is added to the expected lab task completion time CT.

To accommodate different usage scenarios and also changes in the load/capacity/malfunctions/etc. of the laboratory device, according to embodiments, the he step(s) of validating the resource validity data RVD against the expected lab task completion time CT and/or generating a resource validation signal are carried out
  upon loading of the resource 12 onto the laboratory device 1; and/or
  at any time between loading of the resource 12 and start of one or more lab task(s) 22 of the lab task schedule 20; and/or
  upon a change in the lab task schedule 20; and/or
  upon a change in the expected lab task completion time CT of at least one lab task 20; and/or
  upon a change of state of the laboratory device 1 having a potential effect on the expected lab task completion time CT of at least one lab task 20, such as a defective channel affecting throughput; and/or
  upon a change of state of the laboratory device 1 having a potential effect on the resource validity data RVD, such as a change in storage temperature and/or humidity of the resource.

It shall be pointed out that one lab task 22 may have more than one associated resource 12 each having the same or a different resource validity data RVD. On the other hand a resource 12 may be at the same time be associated to more than one lab task 22, each having the same or a different processing time PT.

The following non-limiting examples illustrate certain embodiments of the present subject matter.

Examples

In the following, examples are provided in order to display certain embodiments and to exemplify the subject matter described herein. It is to be understood that also other embodiments are comprised by the scope of the subject matter, as known by the person skilled in the art.

Figure 2:
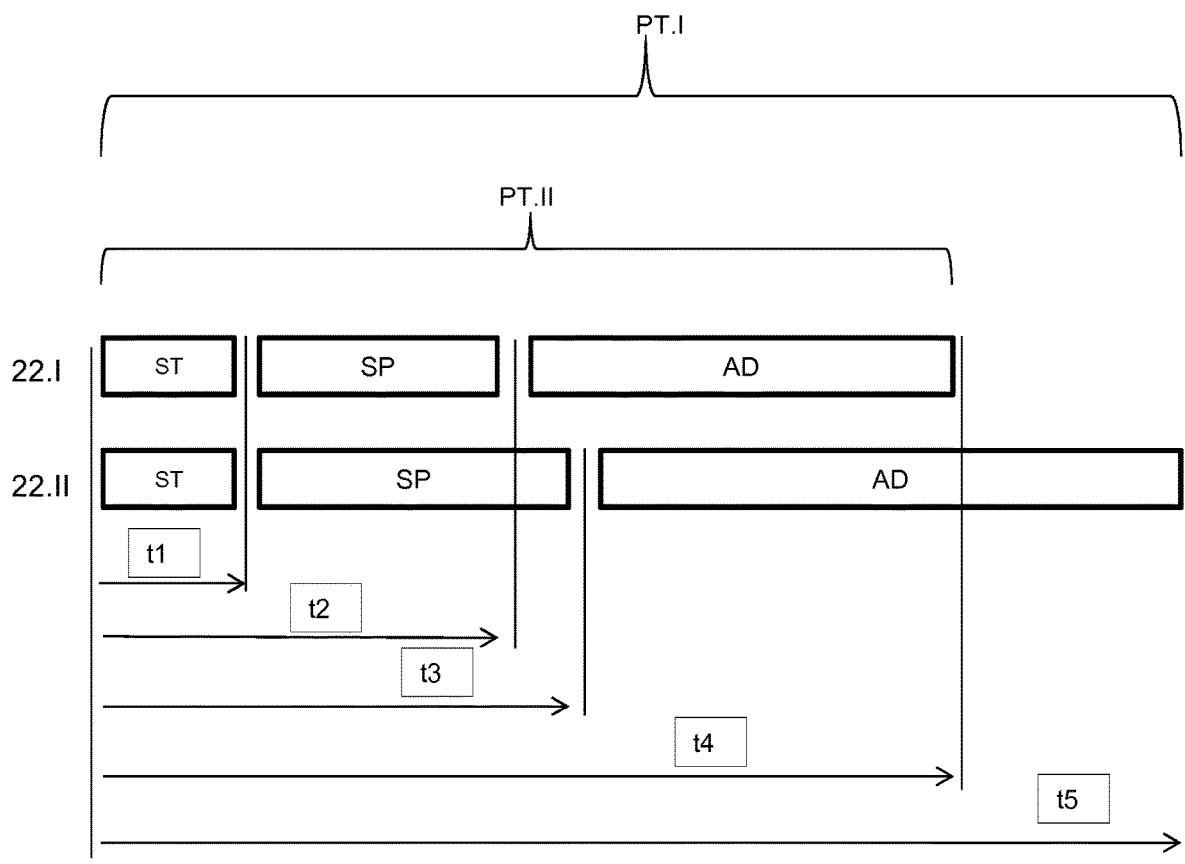
FIG. 2 shows a schematic timeline of an illustrative example for demonstrating the disclosed method.

An embodiment shall be now further described by means of the timeline of FIG. 2 illustrating a specific example.

Loading of Resources on the Laboratory Device

During loading a resource 12 on to the laboratory device 1, the system checks the validity of the loaded resource 12 by checking different expiration times against expected lab task completion time(s) CT. It furthermore takes the processing time PT of all lab tasks 22 on the system into account for the validation. Given, that the lab tasks have different processing times PT, the user can choose if he wants to load a specific resource 12 even if it is only valid throughout a specific lab task.

For example:
resource 12A: valid for the next 3 hours
resource 12B: valid for the next 2 hours
resource 12C: valid for the next 8 hours
lab task 22.I: processing time PT=3.5 hours
lab task 22.II: processing time PT=2.5 hours The resource 12A is only valid for the next 3 hours and the scheduled lab task 22.I has a processing time of at least 3.5 hours. The user will get informed during the loading of resource 12A, that 12A will only be usable for lab task 22.II but not for lab task 22.I. The user can than decide, if he still wants to load the resource 12A, or if he wants to remove it and load a resource with a longer life period e.g. (12C). On the other hand, resource 12B will not be loaded to the laboratory device 1 in any case, due to it cannot be used for any of the lab tasks, even though it would be valid at the moment when the validation is done, but not for the whole processing time PT of any of the lab tasks.

Allocation of Resources for a Lab Task

During allocation of resources 12 for a lab task 22, the process scheduler 5 has to decide if a specific resource 12 can be used for the scheduled lab task 22. That means, the resource 12 has to be valid throughout the specific processing time PT within the planned lab task 22. As shown in the example of FIG. 2, different lab tasks 22.I and II have different processing times PT.I and II during a lab task schedule 20. Depending on the lab task 22 definition, these timings can vary. Due to that, a resource 12A, B or C which might be valid for lab task 22.II might be not valid for lab task 22.I.

On the other hand, the process scheduler 5 has taken into account that not all partial processes (such as sample transfer ST; sample preparation SP and amplification detection AD) of a lab task 22 vary when the processing time PT of two lab tasks 22 are different. It might be that only the amplification and detection AD and the sample preparation SP process of the lab tasks 22.I and II are different but not the sample transfer ST process.

t1: Certain resources 12 must be valid at least until they are pipetted into a P-Plate 48. As the sample transfer ST time is not lab task 22 specific, in this example, the process scheduler 5 can schedule all resources 12 needed which are valid at least for the time span of "t1"

t2: Resources like the consumables P-Plate 48 and Combo Tip Rack 48 are only used until the sample preparation SP phase is over. If the sample preparation SP time is shorter for lab task 22.II than for lab task 22.I (as it is in the given example), the process scheduler 5 can still use consumables which are valid throughout the time of "t2".

t4: The resource AD-Plate 96 has to be valid until the whole lab task is finished. Due to that, the process scheduler 5 can use an AD-Plate 96 which is valid at least for the time span of "t4" even if this AD-Plate 96 would not be usable for run batches with lab task 22.II in the example.

Figure 3:
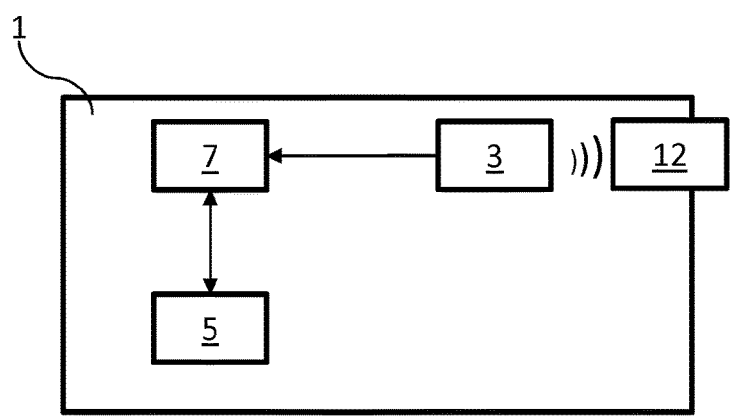
FIG. 3 shows a schematic block diagram of a laboratory device according to a disclosed embodiment.

FIG. 3 shows a schematic block diagram of a laboratory device 1 according to an embodiment, comprising:
a process scheduler 5 storing an lab task schedule 20 comprising at least one lab task 22;
an identifier reader 3 configured to read a resource identifier ID upon the resource 12 being loaded onto the laboratory device 1;
a resource validation module 7 configured to:
retrieve resource validity data RVD corresponding to the identified resource 12;
retrieving an expected lab task completion time CT corresponding to each lab task 22 of the lab task schedule 20;
validate the resource validity data RVD against the expected lab task completion time CT corresponding to one or more lab task(s) 22 of the lab task schedule 20; and
generate a resource validation signal indicative of a result of the validation of the resource validity data RVD.

While the foregoing embodiments have been described in some detail for purposes of clarity and understanding, it will be clear to one skilled in the art from a reading of this disclosure that various changes in form and detail can be made without departing from the true scope of the subject matter. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for validating a resource for a lab task schedule of a laboratory device, the lab task schedule comprising at least two future lab tasks, the method comprising the steps of:
identifying a resource upon being loaded onto the laboratory device;
retrieving, with a resource validation module of the laboratory device, resource validity data (RVD) corresponding to the identified resource, wherein the RVD comprises at least one of: an expiration date and/or time of the resource, an onboard stability time of the resource, and an open stability time of the resource;
retrieving, with the resource validation module, expected lab task completion times (CTs) corresponding to each of the at least two future lab tasks of the lab task schedule;
forward validating, with the resource validation module, the RVD against the expected lab task CTs corresponding to each of the at least two future lab tasks of the lab task schedule;
generating, with the resource validation module, a resource validation signal indicative of a result of the forward validation of the RVD; and allocating the identified resource to the at least one of the future lab tasks if the forward validating step is successful.

2. The method according to claim 1, wherein said resource validation signal corresponding to the resource is indicative of one of the following:
full resource rejection, generated if validation of the RVD is unsuccessful for each future lab task, indicative that the resource is not valid for any of the future lab tasks of the lab task schedule;
partial resource acceptance, generated if validation of the RVD is successful for at least one of the future lab tasks, indicative that the resource is valid for one or more of the future lab task(s) of the lab task schedule; and
full resource acceptance, generated if validation of the RVD is successful for each future lab task, indicative that the resource is valid for each lab task of the lab task schedule.

3. The method according to claim 2, wherein in case the resource validation signal for the resource is indicative of partial resource acceptance, the corresponding resource is allocated to a lab task for which validation of the RVD is successful.

4. The method according to claim 1, wherein the RVD comprises an expiration date and/or time of the resource, the validation of the RVD comprising a comparison of the expiration date and/or time of the resource with the expected lab task CT, the validation being successful if the expected lab task CT does not extend beyond the expiration date and/or time of the resource.

5. The method according to claim 1, wherein the RVD comprises an onboard stability time of the resource, the validation of the RVD comprising a comparison of the onboard stability time with an expected onboard time ranging from loading of the resource to the expected lab task CT, the validation being successful if the expected onboard time does not extend beyond the onboard stability time of the resource.

6. The method according to claim 1, wherein the RVD comprises an open stability time of the resource, the validation of the RVD comprising a comparison of the open stability time with an expected lab task processing time (PT), the validation being successful if the expected lab task PT does not extend beyond the open stability time of the resource.

7. The method according to claim 1, wherein the resource is identified by means of a resource identifier (ID) being read by an identifier reader configured to read the resource ID upon the resource being loaded onto the laboratory device.

8. The method according to claim 7, wherein the resource ID is a radio frequency identifier RFID tag and the identifier reader is an RFID reader.

9. The method according to claim 1, wherein the RVD is retrieved by the resource validation module of the laboratory device from a validity data repository comprised by and/or communicatively connected to the laboratory device.

10. The method according to claim 7, wherein the RVD is retrieved by the resource validation module of the laboratory device from the resource ID, the RVD having been previously stored therein.

11. The method according to claim 7, wherein the RVD is retrieved by the resource validation module of the laboratory device based on resource data retrieved from the resource ID in combination with task data associated with the lab task and/or the lab task schedule.

12. The method according to claim 1, wherein a reserve time is added to the expected lab task CTs in order to provide flexibility with respect to delays in lab task completion.

13. The method according to claim 1, wherein the step(s) of forward validating of the RVD against the expected lab task CTs and/or generating a resource validation signal are carried out both upon loading of the resource onto the laboratory device and at least one additional time, the additional time comprising at least one of the following:
upon a change in the lab task schedule;
upon a change in the expected lab task CT of at least one lab task;
upon a change of state of the laboratory device having a potential effect on the expected lab task CT of at least one lab task; and
upon a change of state of the laboratory device having a potential effect on the RVD.

14. The method according to claim 1, wherein the resource is one or more of the following:
a reagent;
a sample plate; and
a pipetting tip.

15. The laboratory device, comprising:
a process scheduler storing an lab task schedule comprising at least two future lab tasks;
an identifier reader configured to read a resource identifier (ID) upon the resource being loaded onto the laboratory device;
a resource validation module configured to:
retrieve resource validity data (RVD) corresponding to the identified resource;
retrieve an expected lab task completion time (CT) corresponding to each future lab task of the lab task schedule;
forward validate the RVD against the expected lab task CT corresponding to each of the future lab tasks of the lab task schedule;
generate a resource validation signal indicative of a result of the validation of the RVD; and
allocate the identified resource to at least one of the future lab tasks if the RVD is successfully validated.

16. The laboratory device according to claim 15, wherein the resource ID is a radio frequency identifier RFID tag and the identifier reader is an RFID reader.

* * * * *